US011169153B2

(12) United States Patent
Koch et al.

(10) Patent No.: US 11,169,153 B2
(45) Date of Patent: Nov. 9, 2021

(54) METHOD FOR THE NORMALIZATION OF IMMUNOLOGICAL TESTS AND KITS FOR PERFORMING SUCH TESTS

(71) Applicant: Mikrogen GmbH, Neuried (DE)

(72) Inventors: Isabel Koch, Munich (DE); Oliver Boecher, Neuried (DE); Erwin Soutschek, Berg (DE); Steven McNamara, Munich (DE)

(73) Assignee: Mikrogen GmbH, Neuried (DE)

( * ) Notice: Subject to any disclaimer, the term of this patent is extended or adjusted under 35 U.S.C. 154(b) by 477 days.

(21) Appl. No.: 15/743,592

(22) PCT Filed: Jul. 28, 2016

(86) PCT No.: PCT/EP2016/067981
§ 371 (c)(1),
(2) Date: Jan. 10, 2018

(87) PCT Pub. No.: WO2017/017172
PCT Pub. Date: Feb. 2, 2017

(65) Prior Publication Data
US 2019/0079091 A1    Mar. 14, 2019

(30) Foreign Application Priority Data

Jul. 30, 2015 (EP) .................................... 15178989

(51) Int. Cl.
| | |
|---|---|
| *G01N 33/53* | (2006.01) |
| *G01N 33/574* | (2006.01) |
| *C07K 16/18* | (2006.01) |
| *G01N 33/541* | (2006.01) |
| *G01N 33/543* | (2006.01) |
| *G01N 33/577* | (2006.01) |

(52) U.S. Cl.
CPC ........ *G01N 33/57411* (2013.01); *C07K 16/18* (2013.01); *G01N 33/541* (2013.01); *G01N 33/54306* (2013.01); *G01N 33/577* (2013.01); *G01N 2333/025* (2013.01); *G01N 2333/4742* (2013.01)

(58) Field of Classification Search
CPC .... G01N 33/53; G01N 33/543; G01N 33/577; G01N 33/54306; G01N 2333/025; G01N 2333/4742
See application file for complete search history.

(56) References Cited

U.S. PATENT DOCUMENTS

| | | | | |
|---|---|---|---|---|
| 5,500,347 | A * | 3/1996 | Moll ...................... | C07K 16/30 435/7.23 |
| 5,792,617 | A * | 8/1998 | Rotman ........... | G01N 33/57492 435/7.23 |
| 2002/0095073 | A1* | 7/2002 | Jacobs ................ | B01F 13/0088 600/300 |
| 2008/0081348 | A1* | 4/2008 | Feldstein ........... | G01N 33/6893 435/7.92 |
| 2009/0298107 | A1* | 12/2009 | Donndelinger .... | G01N 33/6893 435/18 |
| 2012/0282595 | A1 | 11/2012 | Cheng | |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Smedts, F. et al., "Basal-Cell Keratins in Cervical Reserve Cells and a Comparison to their Expression in Cervical Intraepithelial Neoplasia", *Am. Jrnl. Pathol.* (Mar. 1, 1992), vol. 140, No. 3, pp. 601-612.
Ivanyi, D. et al., "Keratin Subtypes in Carcinomas of the Uterine Cervix: Implications for Histogenesis and Differential Diagnosis", *Cancer Research* (Aug. 15, 1990), vol. 50, pp. 5143-5152.
Mathur, S. P. et al., "Human Papillomavirus (HPV)-E6/E7 and Epidermal Growth Factor Receptor (EGF-R) Protein Levels in Cervical Cancer and Cervical Intraepithelial Neoplasia (CIN)", *Am. Jrnl. Rep. Immunol. Microbiol.* (Oct. 1, 2001), vol. 46, No. 4, pp. 280-287.

* cited by examiner

*Primary Examiner* — Gary Counts
(74) *Attorney, Agent, or Firm* — Smith Patent, LLC; Chalin A. Smith

(57) ABSTRACT

Herein disclosed is a method for the normalization of an immunological test, characterized in that the presence of a comparable amount of cells is determined by a sandwich ELISA test in which the capture antibody includes at least one antibody that binds to at least one keratin selected from among keratin 4, 5, 6, 8, 10, 13 and 18 and the detection antibody includes at least one antibody that binds to the selected keratin.

12 Claims, 10 Drawing Sheets

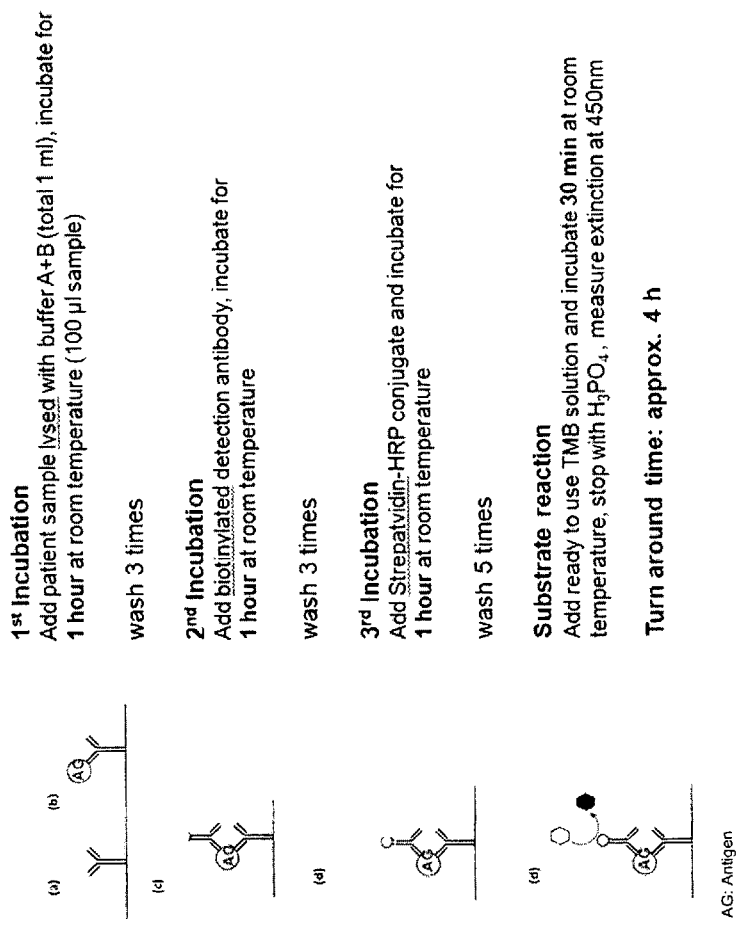

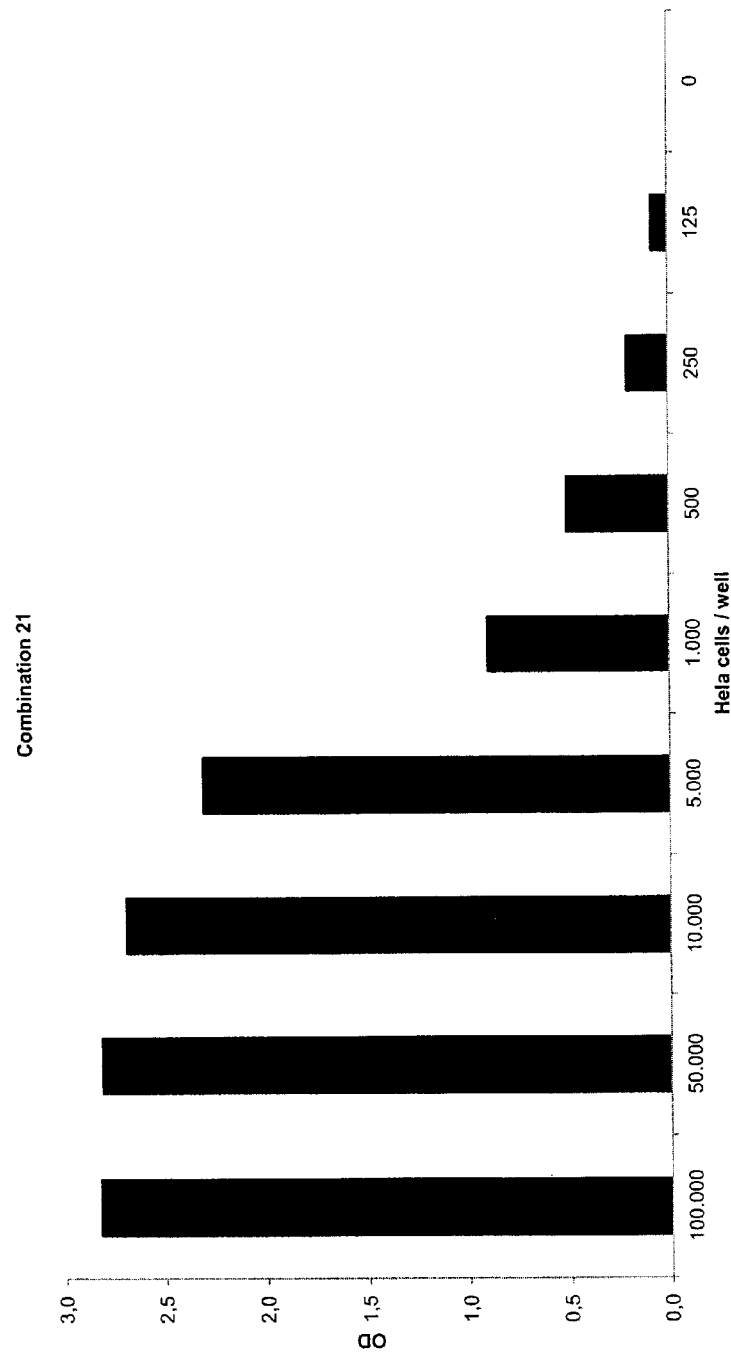

Normal cells

Low-grade changes

Abnormal cells with mild changes at the surface

High-grade changes

Abnormal cells with more serious changes extending to the surface

Cancer

Abnormal cells that have broken through the basement membrane into other tissue

This graph shows keratins 8, 18, and 5 can still be detected in patients (F507-F696) showing various stages of cervical intraepithelial neoplasia (CIN), suggesting that these keratins are not down-regulated throughout the course of disease progression.

METHOD FOR THE NORMALIZATION OF IMMUNOLOGICAL TESTS AND KITS FOR PERFORMING SUCH TESTS

PRIORITY

This application corresponds to the U.S. national phase of International Application No. PCT/EP2016/067981, filed Jul. 28, 2016, which, in turn, claims priority to European Patent Application No. 15.178989.8 filed Jul. 30, 2015, the contents of which are incorporated by reference herein in their entirety.

FIELD OF THE INVENTION

The present invention relates to methods for the normalization of an immunological test as well as tests and kits for use therewith.

BACKGROUND OF THE PRESENT INVENTION

Immunological tests for diagnostic purposes are usually performed on biological samples. Such samples may be body fluids like blood, serum, saliva, urine or liquor. When the samples are taken from a homologous source it can be assumed that the concentration of the agent to be detected is more or less homogeneously distributed among the samples. Difficulties may, however, arise when the sample to be analyzed is cellular material obtained from biopsies, or in particular swabs obtained from mucosa. When a sample is taken from the mucosa, it has to be verified that a comparable and representative number of cells to be analyzed has been obtained in the sample. There are several methods of verifying the presence of a sufficient number of substances to be detected. In nucleic acid related diagnostic methods, usually a so-called housekeeping gene is amplified in order to be sure that a sufficient amount of sample has been obtained.

In immunological tests it is sometimes difficult to perform such a control for several reasons. When the presence of a polypeptide is detected, such polypeptide should be specific for a certain type of cell which is to be analyzed. If this polypeptide is also present on or in other cells the immunological control may not be specific. Another aspect is that the concentration of the control polypeptide to be detected should be continuously and stably present. If cells express one protein in varying amounts depending on the cell cycle or age of the cell, or due to pathologic changes of the cell, it is difficult to standardize the test and obtain comparable values for different samples.

SUMMARY OF THE INVENTION

It is therefore an object of the present invention to provide a method for normalization of immunological tests. Normalization or standardization means that it can be assured that material to be analyzed was indeed contained within the test sample. Furthermore, the method may be used to measure the material to be analyzed in a semi-quantitative manner.

The method for the normalization of an immunological test according to the present invention comprises therefore two tests which are performed on the same sample. One test is a sandwich ELISA test wherein the presence or absence of keratin is determined and potentially quantitatively measured and the other test is a test for the detection of another biomarker in the same sample. The term "biomarker" is understood in a broad sense. Preferably the biomarker is a marker specific for cancer like an immunologically detectable marker of tumor cells which are usually present on the surface of tumor cells.

Although it is preferred that the two tests which are performed on the same sample are both immunological tests it is, however, also possible that one test (regarding the presence or absence of keratin) is an immunological test and the other test is not based on an immunological test principle but for example on the detection and/or quantification of nucleic acids (e.g. PCR test).

In preferred embodiments the two tests are, however, immunological tests. The two tests are performed together which means that the tests are performed at the same time preferably in two different cavities of the microtiter plate. It is also possible to perform the tests one after the other whereby it must be assured that samples used in the two tests are substantially identical.

The method of the present invention is preferably used in immunological tests wherein proteins of the human papilloma virus, preferably the E7 protein, are detected as agent indicative to cancer, in particular cervical cancer. The samples for performing such tests are obtained from mucosa, preferably cervical mucosa of the patients. The invention is illustrated in more detail with reference to cervical cancer. The person skilled in the art will understand, however, that the normalization can be performed with other samples in an analogous manner.

BRIEF DESCRIPTION OF THE FIGURES

FIG. 1 depicts the test principle of a preferred embodiment of the present invention.

FIG. 2B depicts the most preferred combination for detection of cytokeratin in HeLa cells, namely combination 21, which corresponds to 0.05 µg/ml capture antibody and 0.05 µg/ml detection antibody.

DETAILED DESCRIPTION OF THE PREFERRED EMBODIMENTS

Figure 2A:
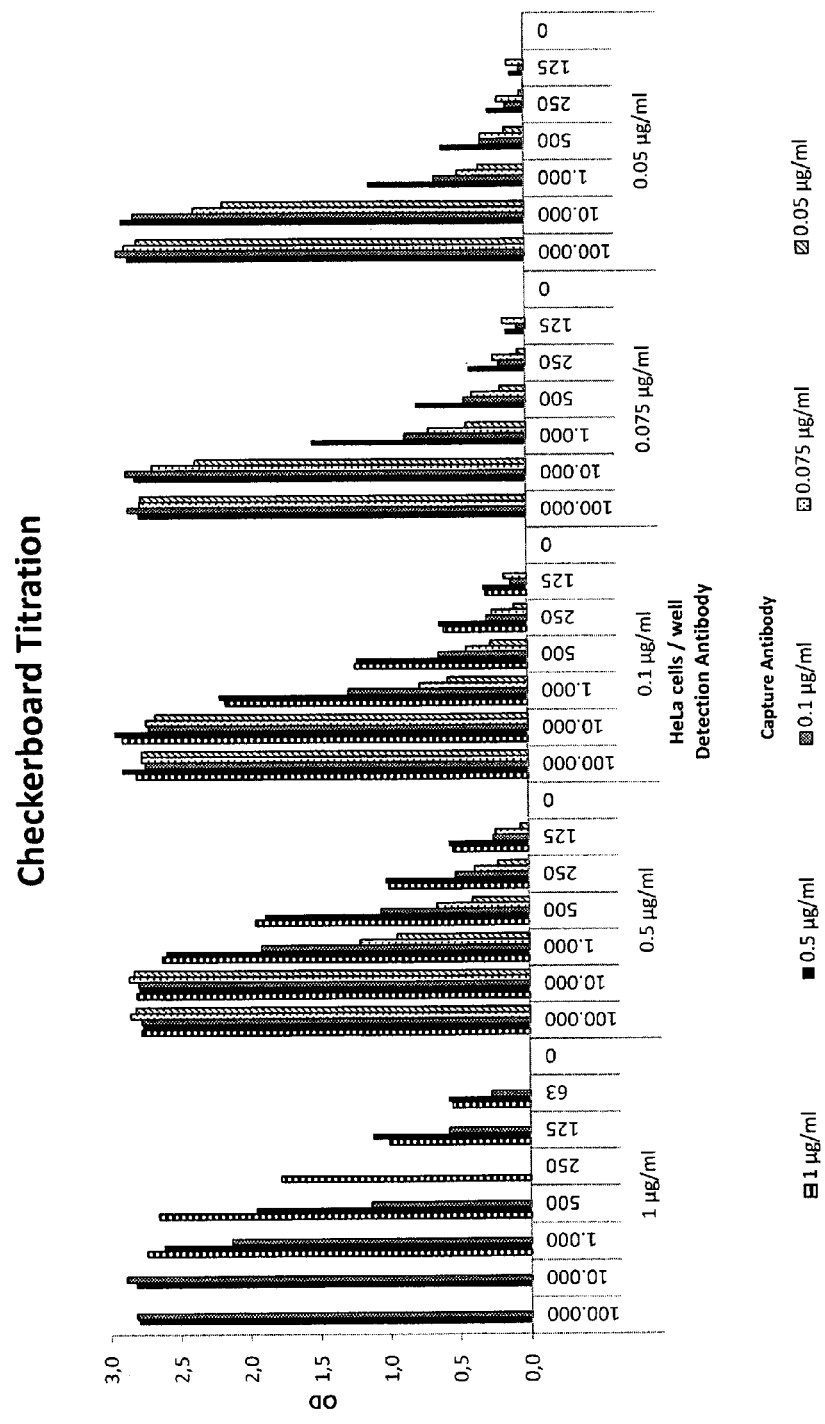
FIG. 2A depicts the results of the checkboard titration experiment described in Example 2.

Cervical cancer is one of the leading causes of cancer morbidity and mortality in women, with more than 98% related to a human papilloma virus (HPV) infection origin.

Cervical cancer screening worldwide is based on cytology (Papanicolaou staining) and/or detection of HPV nucleic acids, i.e. HPV DNA or HPV RNA, in cervical smears.

The cervix is subject to a complex array of physiologic changes over the course of a woman's lifetime. These changes are influenced by multiple factors, both intrinsic (hormone levels, etc) and extrinsic (exogenous infection, etc). Perhaps the most dynamic region of the cervix is the cervical transformation zone, where ectocervix (stratified squamous epithelia) and endocervix (endocervical columnar/reserve cells) meet, and within which lies the squamocolumnar junction (SCJ). The SCJ is constantly evolving through a process called squamous metaplasia (replacement of endocervical cells with squamous cells), and the transformation zone defines the changing area between original SCJ and new SCJ (Cibas E, Ducatman B. *Cytology: Diagnostic Principles and Clinical Correlates*, 4th Edition. W B Saunders, Philadelphia, 2014; Jordan J, Singer A. *The Cervix*, 2nd Edition. Saunders, London; Philadelphia, 2006; Doorbar J, et al. Human papillomavirus molecular biology and disease biology and disease association. *Rev Med Virol* 2015 March; 25 Suppl 1:2-23)

Human papillomavirus is known to infect basal keratinocytes, and for reasons not yet fully understood, it has a tropism for basal/reserve cells found within the cervical transformation zone. In fact, most precancerous lesions and squamous carcinomas originate there. One reason for this may be the proximity of these target cells at the SCJ to the surface. Unlike basal cells of the normal squamous epithelia, which are found buried under several layers of differentiated cells, SCJ cells are simply more easily accessible to the virus. In some cases, persistent infection, leading to overexpression of viral oncoproteins E6 and E7, may inhibit these basal/parabasal cells from normal mitotic arrest and entry into squamous cell differentiation, and instead drive them to proliferate abnormally through stages of high grade cervical intraepithelial neoplasia (CIN) and ultimately cancer.

This knowledge can be exploited when designing a sandwich ELISA to screen for E7 levels in infected cells, but more importantly when designing a standardizing test for the E7 ELISA itself. The stratified squamous epithelium of the cervix consists of multiple layers of cells, from differentiated (intermediate, superficial) down to undifferentiated (basal, parabasal) at the basement membrane. In a typical cervical sampling, only the most superficial layers are scraped away for analysis. Incorrect sampling of superficial layers only could easily lead to false results. Based on the knowledge of HPV carcinogenesis, it would seem absolutely critical that each sample contains cells from within the SCJ/cervical transformation zone, as this is the best chance to catch endocervical/reserve/basal/parabasal cells due to their proximity to the surface. Current Pap cytology guidelines require a minimum of 10 endocervical or squamous metaplastic cells be seen on smear to signify that the transformation zone has been sampled, thus assuring better test accuracy. When designing a measurable assay such as an ELISA, this becomes even more critical, especially in patients who are truly negative for CIN progression and/or carcinoma. Without proper transformation zone sampling in all cases, the test becomes limited.

To ascertain that a proper sampling has been taken, a test must screen for a molecular marker specific to the target cells in question. One marker specific for squamous and endocervical cells is keratin. Keratins are intermediate filament proteins manifesting a high degree of molecular diversity: Whereas some are important for mechanical stability and integrity of cells, others are involved in regulatory and intracellular signaling pathways. Over 50 functional keratin genes exist (Moll R, et al. The human keratins: biology and pathology. *Histochem Cell Biol* 2008 June; 129(6):705-733).

US 2012/0282595 describes a method for quantifying HPV protein expression in a clinical sample whereby cells from the sample are fixed to the holes of a microtiter plate. By applying buffers containing detergent the cell membrane is made permeable for antibodies directed against E6 or E7, respectively. By adding an anti-antibody and a subsequent colour generating reaction the amount of E6 and E7 shall be quantified. It is suggested to normalize the number of cells tested in each well of a microtiter plate. The proposed methods of normalization are, however, not specific.

It has been thirty years since the link between HPV and cervical cancer has been discovered, and in that time, relatively little has been published concerning the dynamics of keratin expression in the cervix and in cervical cancer. Despite this deficiency in literature, some early studies have shown that keratin expression is highly specific depending on the stage of cellular differentiation, and location within the endocervix or the stratified squamous epithelium of the ectocervix. For example, maturation keratins, those seen in differentiated cells of the intermediate and superficial layers, include such keratins as 4, 10, and 13. Meanwhile, it has been demonstrated that keratin 5 is found in reserve, basal, and parabasal cells (Smedts F, et al. Basal cell keratins in cervical reserve cells and a comparison to their expression in cervical intraepithelial neoplasia. *Am J Pathol* 1992 March 140(3):601-612) while keratins 8 and 18 are also found in basal and reserve cells, and additionally in endocervical cells (Ivanyi D, et al. Keratin subtypes in carcinomas of the uterine cervix; implications for histogenesis and differential diagnosis. *Cancer Res* 1990 Aug. 15; 50(16):5143-52). These two articles differ, however, from the present invention since the antibodies against keratins were used in immunofluorescence techniques on cryostat sections of human tissues and not in immunological tests. In those articles the antibodies against keratins were used for differential diagnosis and not for the normalization of an immunological test.

According to the present invention keratin candidates were used which showed the best evidence of a reliable expression pattern in undifferentiated squamous cells (parabasal, basal, reserve, immature squamous metaplastic) in healthy patients. Secondarily, it was important to select keratins whereby the expression of these proteins is maintained throughout the course of lesion progression and/or cervical carcinoma. Studies based on keratin phenotyping have not only suggested that the progenitor cell of high grade CIN lesions and cervical carcinomas is the basal/reserve cell, they have also shown that there is generally no down regulation of such basal keratins as 8 and 18 in tumors, and of basal keratin 5 in progressive CIN lesions.

Keratin 5 is found in parabasal and basal cells, and quite possibly reserve cells. Keratins 8 and 18 are found in reserve, basal, and endocervical cells. There may be more overlap within these cell types, but what we do know is these keratins are not found in differentiated cells, and this is of key importance. Additionally, keratins 8 and 18 can be found in endocervical columnar cells, another product of the reserve (stern) cell.

It is assumed that the epithelial reserve cells of the cervix may be the primary target cells for the high risk HPV infections that lead to intraepithelial lesions and cancer. These slow-cycling epithelial stem cells—which are located at the transformation zone of the cervix between endo- and ectocervix—differentiate into either a columnar or a stratified-differentiating epithelium. Nevertheless, it is assumed that HPV infection can occur in any of the (epithelial) cell types close to the basal lamina, including the columnar cells of the endocervix and glands, the reserve cells/stem cells that maintain the columnar and stratified epithelium, and the transiently amplifying and more rapidly dividing cells that have begun their first commitment to differentiation.

FIGS. 6A to 6D show schematically the transformation of the cervix cells whereby stepwise the cells are transformed to a malignant state.

Since the composition of cervical smears is heterogeneous and the samples contain, besides the epithelial cells of the cervix, mucus, blood, immune cells, and the commensal flora of the vagina, it is the object of the present invention to provide a method for normalizing the presence of epithelial cells in cervical samples.

Some HPV nucleic acid detection tests use so-called housekeeping genes such as β-globin or human histone 2 for cellular validity of the samples. These house-keeping genes fall short in discriminating between epithelial cells and all other cell types such as leukocytes in the sample. However, the number of epithelial cells in the cervical sample remains unknown. In contrast, cytology is based on visual inspection of the sample by a cytologist, which requires ample experience of the person performing the analysis.

Tests such as immunohistochemistry have been done on tissue looking for these keratins, but no ELISA method testing for these keratins in cervical samples has been published. Thus, it would be impossible to say at the start if these keratins are even measurable in a cervical sample, especially taking into account sampling procedure error/incorrect cell population. It was uncertain whether the amount of keratin from target cells (basal/parabasal, etc.) would be enough to generate a signal.

Due to keratin expression overlap in cells, an ELISA cannot tell us which cells (EC, basal, parabasal) the signal is coming from, this is why it is important to have all three antibodies (against keratins 5, 8, and 18) in this range of undifferentiated cells (including endocervical (EC)), all of which HPV can establish infection and possibly produce high E7 levels (adenocarcinoma in EC). Things get a bit more complex when considering hormonal effects and changes (estrogen stimulating normal squamous differentiation, progesterone inducing squamous atrophy, etc.), patient age, or use of IUDs, etc., but all in all, the target cells defined in this assay still remain the same.

It is an object of the present invention to provide by the method of normalization evidence that the sample to be analyzed does in fact contain such cells which may potentially contain the substance to be detected. In a preferred embodiment it is an object of the present invention to make sure that the sample contains a sufficient number of cervical cells which may have been infected by human papilloma virus. In a preferred embodiment the method of the present invention is so sensitive that it can be used in a semi-quantitative manner in order to determine whether a comparable amount of relevant cells is present in each sample.

The present invention provides therefore a method for the normalization of an immunological test wherein the presence of a comparable amount of cells is determined by a sandwich ELISA test wherein the capture antibody is at least one antibody which binds to keratin and the detection antibody is at least one antibody which binds to keratin. A test that screens for keratins 5, 8, and 18 is preferably used to predict the validity of cervical sampling and furthermore, E7 test reliability.

The epidermis is a multilayered (stratified) epithelium composed largely of keratinocytes, so named, because their characteristic differentiated activity is the synthesis of intermediate filament proteins called keratins, which give the epidermis its toughness.

Keratins (K) are the largest subgroup among the intermediate filament (IF) family of cytoskeletal proteins. All IF proteins, including keratins, have a characteristic "rod" domain that is flanked by N-terminal "head" and C-terminal "tail" domains. The known human keratin functional genes, which exclude hair keratins, are grouped into relatively basic type II (K1-K5/K6a-K6c/K7/K8/K71-K80) and relatively acidic type I (K9/K10/K12-K20/K23-K28) keratins. Epithelial cells express at least one type I and one type II keratin in an epithelial cell-specific manner. For example, "simple" (single-layered secretory or absorptive) epithelia as found in the liver, pancreas, and intestine express primarily K8/K18 (with variable levels of K7/K19/K20), whereas keratinocytes express primarily K5/K14 basally and K1/K10 suprabasally. In the liver, adult hepatocytes express K8/K18 exclusively, whereas biliary epithelia express K7/K8/K18/K19. Simple epithelial keratins carry out a number of functions, including cytoprotection (for example, from apoptotic injury); protein targeting and synthesis; and modulation of mitochondrial subcellular organization, size, and function.

There are two types of cytokeratins: the acidic type I cytokeratins and the basic or neutral type II cytokeratins. Cytokeratins exist as heterotetramers composed of two type I and two type II keratin subunits. At least one member of the acidic family and one member of the basic family is expressed in all epithelial cells.

Apart from K8/K18, keratins K7 and K19 are "additional" (secondary) and also widely distributed simple-epithelial keratins which are frequently but not always co-expressed. They typically occur as a keratin pair in simple ductal epithelia such as bile and pancreatic ducts ("ductal-type" keratins). However, in several epithelia lacking K7 such as intestinal epithelium, the type I keratin K19 must form a pair with the sole type II keratin K8.

The type I keratin K19 is the smallest keratin and is exceptional since it widely lacks the non-a-helical tail domain typical for all other keratins. It may have evolved from keratinocyte keratins. As detectable by several specific and well-tested monoclonal antibodies, K19 exhibits a rather broad tissue distribution. It is expressed in most simple epithelia (excluding parenchymatous cells such as hepatocytes, pancreatic acinar cells, and renal proximal tubular cells), notably in various ductal epithelia, in small and large intestinal epithelium, in gastric foveolar epithelium, and in mesothelium. Furthermore, it is present in most cells of pseudostratified epithelia and urothelium as well as in basal cells of non-keratinizing stratified squamous epithelia.

It is expressed in most simple epithelia (excluding parenchymatous cells such as hepatocytes, pancreatic acinar cells, and renal proximal tubular cells), notably in various ductal epithelia, in small and large intestinal epithelium, in gastric foveolar epithelium, and in mesothelium. Furthermore, it is present in most cells of pseudostratified epithelia and urothelium as well as in basal cells of non-keratinizing stratified squamous epithelia. The expression of K19 may be induced in certain epithelia that normally lack this keratin by pathological alterations. K19 induction is also observed in suprabasal stratified squamous epithelial cells of oral mucosa with epithelial dysplasia, but also with inflammation, so that K19 cannot be used as a specific marker for dysplasia in oral mucosa. In carcinomas, K19 is widely expressed in both adenocarcinomas and squamous cell carcinomas and therefore is not extensively used as an immunohistochemical marker for carcinoma subtyping. The detection of soluble K19 fragments in the serum released by carcinoma cells by the CYFRA 21-1 assay has found broad clinical application as a marker to monitor treatment and evaluate response to therapy and has proven particularly useful in the case of squamous cell carcinomas of the lung.

The keratin expression pattern of squamous cell carcinoma was found to be complex with changes of in the keratin profile during progress of the disease. Additionally, the keratin expression of the ectocervical epithelium, endocervical epithelium and the reserve/stem cells differs significantly. It is an important aspect of the present invention that under both physiologic and pathologic conditions, cytokeratins are detectable in cervical samples (Smedts et al. American Journal of Pathology (1992), 497-511).

The expression spectrum of K5 and K14 in tumors corresponds well to the patterns in normal epithelia. Thus, most squamous cell carcinomas, as well as malignant mesotheliomas strongly express these keratins whereas little, focal, or no expression is found in adenocarcinomas. Hence, these keratins, in particular K5, have found several lines of diagnostic application in pathology, which has been aided by the availability of a highly sensitive and specific, robust, paraffin-suited MAb. Pertinent examples are the recognition and diagnosis of poorly differentiated squamous cell carcinomas, including micrometastases in lymph nodes, of undifferentiated nasopharyngeal carcinomas which may be diagnostically difficult due to their dissociated growth pattern, and of malignant mesotheliomas. Thus, K5 immunostaining allows the distinction of the small cell type of squamous cell carcinoma of the lung, which is K5+, from a small cell carcinoma or a poorly differentiated adenocarcinoma, both of which are K5–, and the distinction of a malignant mesothelioma of the pleura (K5+) from a pulmonary adenocarcinoma with pleural involvement (K5–). In well and moderately differentiated squamous cell carcinomas, K5 is preferentially localized in the peripheral layers of the tumor cell formations, corresponding to the K5 expression in the basal cell layer of normal stratified squamous epithelia. Focal K5 expression may be observed in certain adenocarcinoma types, notably in adenocarcinomas of the endometrium, the ovary, and the pancreas, which seems to be related to their potency for focal squamous differentiation. Much interest has evolved regarding the role of K5 in breast pathology in several aspects, including the identification of myoepithelial cells, the classification of proliferative lesions, and the recognition of a certain subtype of invasive ductal breast carcinoma. In prostate pathology, the diagnosis of prostatic adenocarcinoma is supported by the immunohistochemical demonstration of absence of K5-positive basal cells.

The present invention relates to a test for the simultaneous detection of several types of cytokeratins (preferably selected from type 4, 5, 6, 8, 10, 13, and 18) in a biological sample whereby in a sandwich ELISA as capture antibody one monoclonal is used which binds preferably to at least seven different types of cytokeratin. As detection antibody the same monoclonal antibody may be used. It is, however, also possible to use different monoclonal antibodies as capture and detection antibody.

Since the sequences of the different keratins are known, suitable antibodies for performing the method of the present invention can easily be prepared. In case antibodies reacting with several different keratins are desired it is preferred to use a consensus sequence as polypeptide for the immunization. If on the other hand antibodies reacting only with a specific type of keratin are desired a sequence for immunization may be selected which is unique for this type of keratin. When such specific sequences are used for immunization it is preferred to produce the antibodies as monoclonal antibodies using the well-known hybridoma technology. Hybridoma technology can be performed with different animals like mice, rats, rabbits or camels.

In an alternative embodiment polyclonal antibodies against keratins can be used. For the immunization of laboratory animals like rabbits, sheep, goats, donkeys or horses, either one purified keratin or a mixture of several different keratins can be used for immunization.

The immunological test of the present invention is based on the principle of a so-called sandwich ELISA. ELISA is the abbreviation for "enzyme linked immuno sorbent assay". In the test "sandwich" the antigen can be considered as the "ham" and the capture and detection antibodies are the two sides of the roll. In a sandwich ELISA there are capture antibodies, which are usually attached to the surface of the reaction well. In the present invention the capture and detection antibody is preferably a pan-keratin monoclonal antibody which was produced by immunization of mice with a cytoskeleton preparation from A431 cells (epidermoid carcinoma).

According to the method of the present invention one type of antibody is used as capture antibody which is attached to the solid phase of the kit. In a preferred embodiment microtiter plates having 96 wells are used. The titer plates are coated with an anti-human keratin antibody which is preferably a monoclonal mouse anti-human keratin antibody. In a particularly preferred embodiment such antibody is specific for at least one of the keratins 4, 5, 6, 8, 10, 13 and 18.

The detection antibody which may either be the same antibody as the capture antibody or another antibody is provided in a kit for performing the method of the present invention. In an alternative it is also possible to use a mixture of different monoclonal or polyclonal antibodies specific for keratin as capture or detection antibody.

The detection antibodies are linked to means which allow the visualization of the sandwich consisting of the capture antibody, the target (keratin) to be detected in the sample and the detection antibody. Such means may be either chemically linked to the detection antibody or alternatively the visualization may be performed by using an anti-antibody specific for the detection antibody. Very frequently the linkage is performed by the interaction of biotin-streptavidin whereby an enzyme may be coupled to the detection antibody which performs a reaction between a substrate and a product whereby substrate and product have different colours. The colour formation can be measured preferably with a spectrophotometer at a suitable wavelength.

In the diagnostic test method the biological sample to be tested is brought into the wells which are already coated with the monoclonal capture antibody. The biological sample is preferably a sample obtained from the cervix, preferably the cells of the cervix. In a preferred embodiment the cells of the biological sample are lysed preferably by the action of a lysis buffer which may contain a detergent. Since human papilloma virus can also be involved in other cancer forms such as head and neck cancer (oropharyngial cancer) or anal cancer the biological sample can also be obtained from patients suffering from such cancers. For analysis of cervical samples, e.g. regarding the presence or absence of HPV, it is important to know whether a sufficient amount of epithelial cells are in the biological sample or not.

The antigen, namely the cytokeratin of type 4, 5, 6, 8, 10, 13, and 18 (if present), binds to the capture antibody. Afterwards unbound material is washed away. For the detection of the cytokeratin a so-called detection antibody is used. According to a preferred embodiment of the present invention the detection antibody is identical to the capture antibody.

The detection antibody is responsible for the test signal. In a preferred embodiment the monoclonal antibody is purified and biotinylated or HRP-labeled. The biotinylation allows the link of the detection antibody to a label which forms a detectable signal.

It is also an embodiment of the present invention to provide a kit for performing the method for normalization. Such kits are usually distributed to test laboratories and comprise all required means for performing the method for normalization. Usually the kit comprises microtiter plates for performing an ELISA test. The microtiter plates are already coated with the capture antibody whereby potential unspecific binding sites are already pretreated in order to avoid any unspecific binding to the solid phase. Furthermore, the kit may comprise buffer solutions or prepared mixtures of chemicals which can be reconstituted with distilled water to prepare such buffering and/or washing solutions. Usually the detection antibody is also provided in a storable, e.g. lyophilized form. The test kits are in a form which can be easily used by persons trained to work in a laboratory.

In preferred embodiments the label forms the signal which is preferably created by the action of an enzyme which converts a precursor to a product which results, for example, in a colour change of the reaction medium. Very frequently ELISA tests are performed on titer plates having several (e.g. 96) wells. The titer plates are part of the kit for performing the immunological test.

In an alternative embodiment the sandwich ELISA can be performed with beads to which the capture antibody is linked. In this embodiment the bead to which the capture antigen is linked is brought into contact with the biological sample. After incubation the beads to which the antigen (keratin) was bound is removed from the sample and washed. Then the beads are brought into contact with the detection antibody and means for detecting. After a further washing step the colour reaction may take place and measurement preferably with a spectrophotometer can be performed. The advantage of using a bead based sandwich ELISA test is that the beads can easily be removed from the reactive mixture either by centrifugation or with the help of magnetic forces when the beads contain metallic iron for example in the core of the beads.

According to the present invention it is possible to attach as capture antibody only one type of monoclonal antibody into one single well. The advantage of using the identical antibody for detection is the simplicity of the method.

One embodiment of the present invention relates to diagnostic test kits which are suitable for performing the diagnostic test of the present invention. Usually such kits contain the monoclonal antibodies which function as capture antibodies linked to a solid phase preferably in a reaction well. Alternatively, however, the capture antibodies can be linked to beads which may be made from plastic material (e.g. sterol). The detection antibody is usually contained within the test kit in a suitable form. In a preferred embodiment the detection antibody is present in a ready to use form or in a lyophilized form which can be reconstituted with suitable buffer solution. Test kits are usually provided with means required for performing the immunological test method. Such means include buffer and reagents which allow the generation of a signal. Such reagents may be for example anti-antibodies linked to an enzyme which in turn generates a colour signal from a precursor.

At present, more than 20 different cytokeratins have been identified, with a molecular weight between 40 and 68 kDa. There are two types of cytokeratins: the acidic type I cytokeratins and the basic or neutral type II cytokeratins. Cytokeratins are usually found in pairs comprising a type I cytokeratin and a type II cytokeratin. Basic or neutral cytokeratins include CK1, CK2, CK3, CK4, CK5, CK6, CK7, and CK8. Acidic cytokeratins are CK9, CK10, CK12, CK13, CK14, CK16, CK17, CK18, CK19 and CK20.

In a preferred embodiment of the present invention at least one of the keratins 5, 8 and 18 are used in the test. In a more preferred embodiment at least two and in a particularly preferred embodiment the three keratins 5, 8 and 18 are used in the test in order to enhance the reliability of the normalization test.

It is an important aspect of the present invention that by using one monoclonal antibody as capture and detection antibody it is possible to bind the antigen to be identified, namely the cytokeratin from at least seven cytokeratin types which are predominately expressed in normal and cancerogenous tissue (Smedts et al, 1992).

The test principle of a preferred embodiment is shown in FIG. 1. For performing a diagnostic test according to the invention a suitable test kit is prepared. At the surface of the wells of the reaction holes the capture antibody is attached to each well of the titer plate. Then a biological sample obtained from a patient is pipetted into the well. The sample is usually lysed with a special lysis buffer and incubated for a sufficient time, preferably one hour, at room temperature. This allows the binding of potential cytokeratin antigen to the capture antibody. Subsequently the wells are washed several times, preferably three times.

In the third step the wells are incubated with the detection antibody and the reaction mixture is incubated for a sufficient time, preferably around one hour at room temperature. In order to purify the well from unbound material the well is washed preferably three to six times with a washing buffer.

In the next step the signal producing means is linked to the detection antibody. This can preferably be done by a streptavidin-biotin binding. Then the wells are washed several times in order to avoid any non-specific reaction.

Finally the signal is created, usually by adding a colourless substrate which is converted by the action of the signal performing means (enzyme) into a coloured product. For example a TMB solution can be used for the development of the colour. After a certain time, usually about 30 minutes, the reaction is stopped by addition of a stopping agent (e.g. $H_3PO_4$) and the extinction is measured at a suitable wavelength, preferably at about 450 nm.

In a particularly preferred embodiment of the present invention the method for normalization is used together with another test whereby an indicator for cervical cancer is determined. Such test is preferably also a sandwich ELISA test. A suitable indicator for cervical cancer may be for example an oncoprotein of human papilloma virus like the E6 or preferably E7 oncoprotein as described for example by Lee et al., J. Immunol. 2001, 167, 497-504. The advantage of using the normalization method together with an immunological assay concerning the presence of oncoprotein E6 and/or E7 of human papilloma virus is that by the standardization method it is confirmed that the sample in fact contains cells which may produce an oncogen.

If the test relating to an oncoprotein is performed without the method for the standardization according to the present invention and a negative result is obtained there are at least two ways of interpretation of the test result. One interpretation is that the patient does not suffer from cervical cancer or a high grade squamous intraepithelial lesion. The alternative explanation is that in the sample obtained by a swab of the cervix obtained from the gynecologist no relevant cells have been collected. This second alternative leading to a potentially false-negative result can be excluded by using the method of the present invention.

Preferred embodiments of the present invention are described in more detail in the examples and the figures.

EXAMPLE 1

Performing a Sandwich ELISA Test

Initially, 96-well microtiter plate wells were coated with mouse anti-human keratin monoclonal antibody (obtained from Cell Signaling Technology, product #4545S). The antibody is specific for keratins 4, 5, 6, 8, 10, 13 and 18, and the coating concentration has been optimized at 0.05 µg/ml for this assay. In preparatory experiments a range of 0.01 to 1.0 µg/ml has been tested. Best results were obtained with 0.05 µg/ml. Subsequent cell/sample lysis, addition of defined amount of sample (100 µl) to plate wells, and incubation (1 hour) enable specific binding of keratin proteins to coated antibodies. A washing step is followed by the addition of detection antibody (100 µl). In this case a biotinylated mouse anti-human keratin monoclonal antibody (obtained from Cell Signaling Technology, Product #4279) was used, which has also been optimized at 0.05 µg/ml. During another incubation step (1 hour), the biotinylated antibody binds keratin that has already been captured by the assay. A second washing step succeeded by the addition of streptavidin-horseradish peroxidase (HRP) (100 µl), which binds biotin, if present, with great affinity. After incubation (1 hour) and a third washing, substrate TMB (100 µl) was added. During this final incubation step (30 minutes), HRP-catalyzed reaction of the substrate TMB resulted in a blue color of the solution. The reaction was finally stopped with 100 µl of Stop Solution (blue changes to yellow), and the optical density (O.D.) was read on a spectrophotometer at 450 nm.

EXAMPLE 2

Set Up of the Assay

In order to test the feasibility of the chosen antibody to detect cytokeratin in the ELISA system, different concentrations for capturing as well as for detection were used and a checkerboard titration was performed (Table 1).

Afterwards, lysates of a cervix carcinoma cell line (HeLa; lysates with 100,000, 10,000, 5,000, 1,000, 500, 250, 125, and 63 cells per well) were added to the plate to obtain information about the sensitivity of the assay. Additionally, buffer without any cell lysates served as a blank (negative) control. As detection antibody the identical antibody as used for capturing was used. The antibody was biotinylated to obtain best possible sensitivity In the test cell lysates of the cervix carcinoma cell line HeLa were used. The cells were cultured as described by the supplier, stored in a fixative (ThinPrep) for at least 24 hours to mimic sample conditions and lysed via a special lysis buffer before application in the assay.

The results of the experiment can be seen in FIG. 2A. The most preferred combination for detection of cytokeratin in HeLa cells is combination 21 (FIG. 2B) which corresponds to 0.05 µg/ml capture antibody and 0.05 µg/ml detection antibody.

EXAMPLE 3

Control Experiments with Cell Lines

Figure 3A:
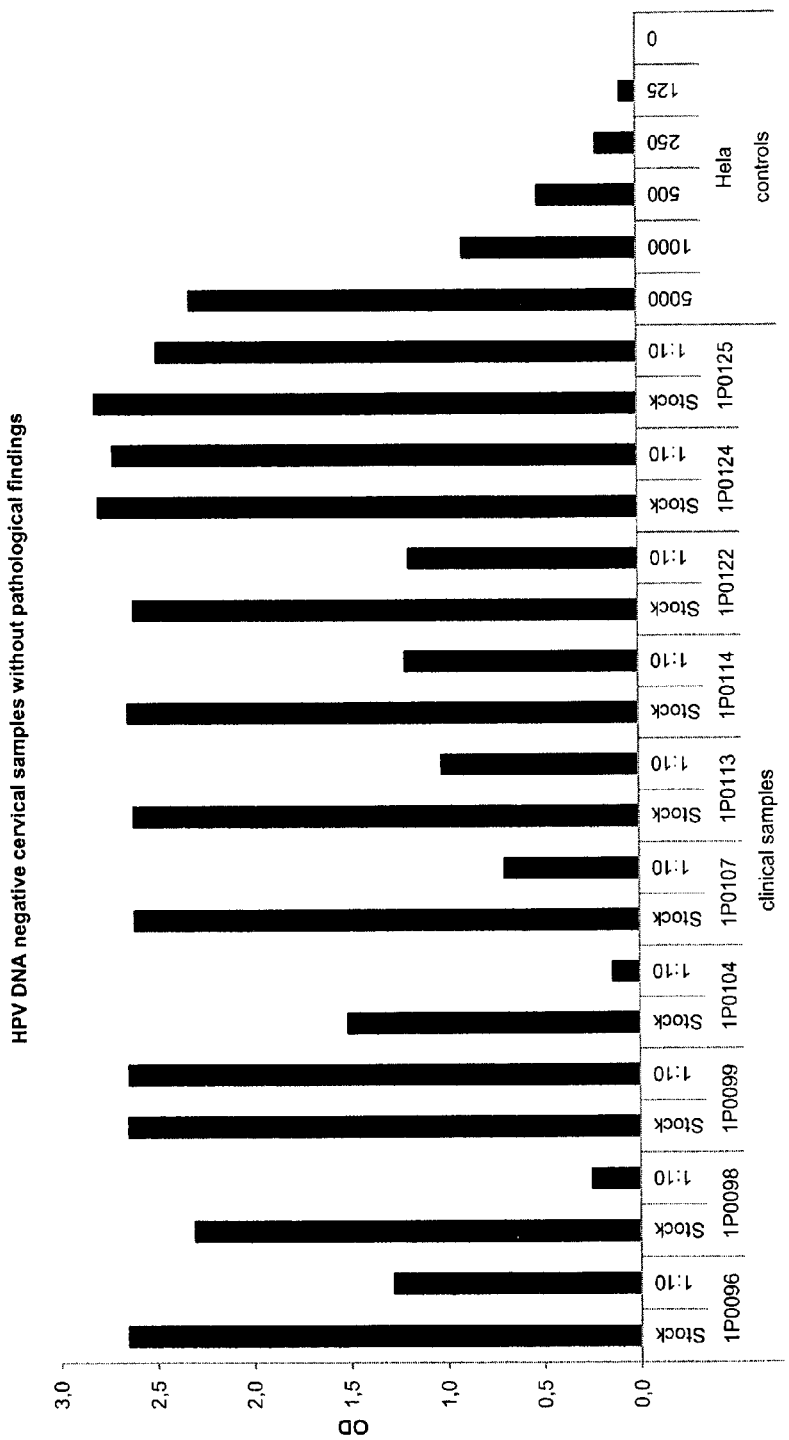
FIG. 3A depicts the results of the control experiments with cell lines described in Example 3.

Control experiments with combination 21 revealed signals clearly over background with cell lysates of at least 125 HeLa cells and in lysates of HPV DNA negative cervical samples without clinical findings (FIG. 3A). No signals were detected for the buffer control (blank). Further control experiments (data not shown) were performed with other carcinoma cell lines.

The cervix samples were measured undiluted and as a 1:10 dilution. Serial dilutions of HeLa cells lysates were used as a pseudo calibration curve and the amount of cells was back calculated via 4 parameter logistic model. Furthermore, dilution linearity is given with a coefficient of correlation of 0.941 (Table 2).

TABLE 2

| pseudo calibration curve with HeLa cell lysates | | | |
|---|---|---|---|
| Hela cells/well (nominal) | Combination 21 [OD] | Cell no. back calculated | Coefficient of correlation |
| 10,000 | 2.696 | 9994 | 0.941 |
| 5,000 | 2.311 | 5010 | |
| 1,000 | 0.904 | 981 | |
| 500 | 0.513 | 536 | |
| 250 | 0.212 | 235 | |
| 125 | 0.082 | 103 | |
| 0 | 0.000 | 0 | |

TABLE 1

| checkerboard titration (schematically) | | | | | | |
|---|---|---|---|---|---|---|
| Concentration of the antibody | | Detection antibody | | | | |
| | | 1 µg/ml | 0.5 µg/ml | 0.1 µg/ml | 0.075 µg/ml | 0.05 µg/ml |
| Capture antibody | 1 µg/ml | Combination 1 | Combination 2 | Combination 3 | Not tested | Not tested |
| | 0.5 µg/ml | Combination 4 | Combination 5 | Combination 6 | Combination 7 | Combination 8 |
| | 0.1 µg/ml | Combination 9 | Combination 10 | Combination 11 | Combination 12 | Combination 13 |
| | 0.075 µg/ml | Not tested | Combination 14 | Combination 15 | Combination 16 | Combination 17 |
| | 0.05 µg/ml | Not tested | Combination 18 | Combination 19 | Combination 20 | Combination 21 |

EXAMPLE 4

Control Experiments with Cervical Samples

Figure 3B:
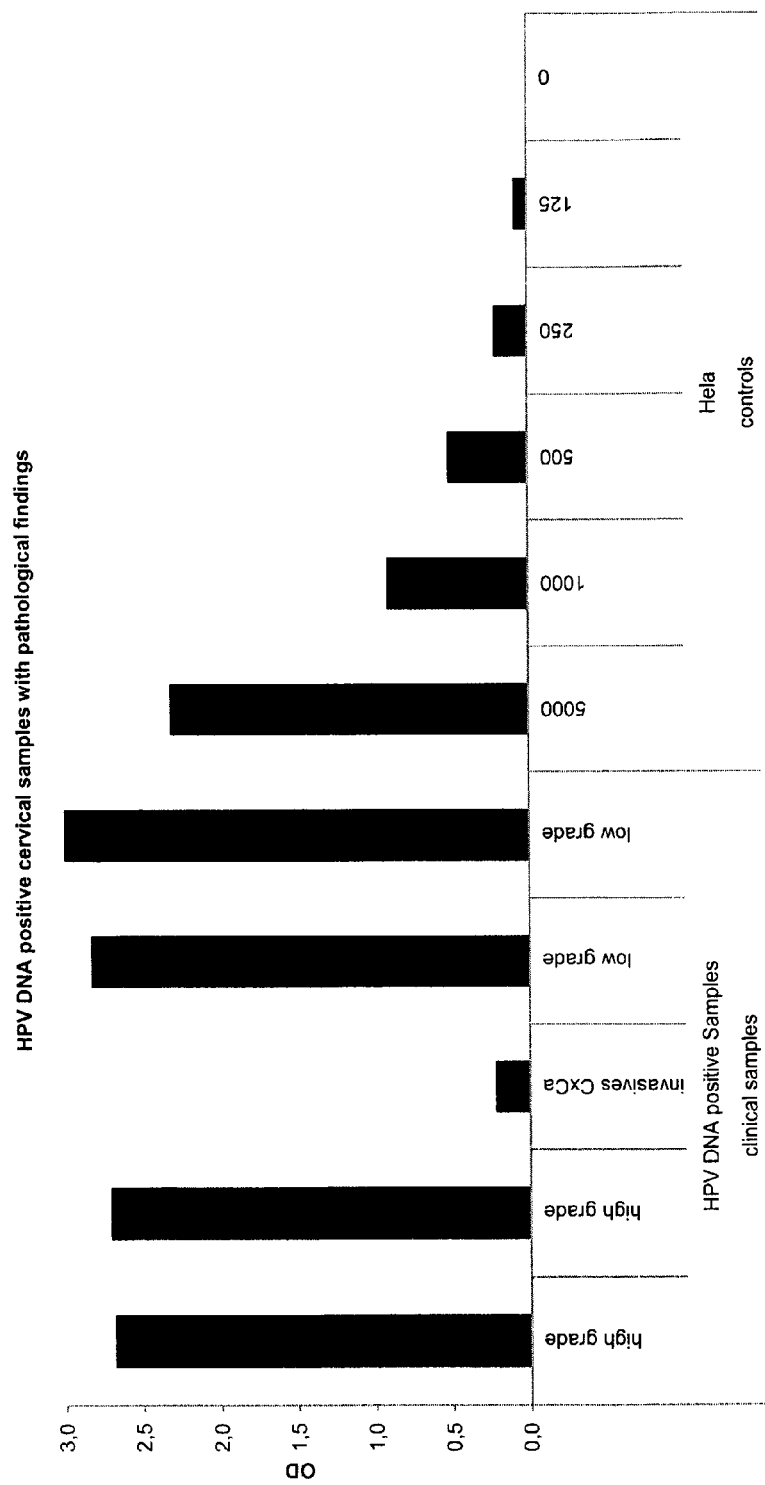
FIG. 3B depicts the results of the experiments with HPV DNA positive, clinically abnormal cervical samples described in Example 4.

Also in control experiments with HPV DNA positive, clinically abnormal cervical samples, cytokeratin level clearly over background were detectable (FIG. 3B). These samples showed low and high grade lesions or an invasive cervix carcinoma as confirmed by histology.

Figure 4A:
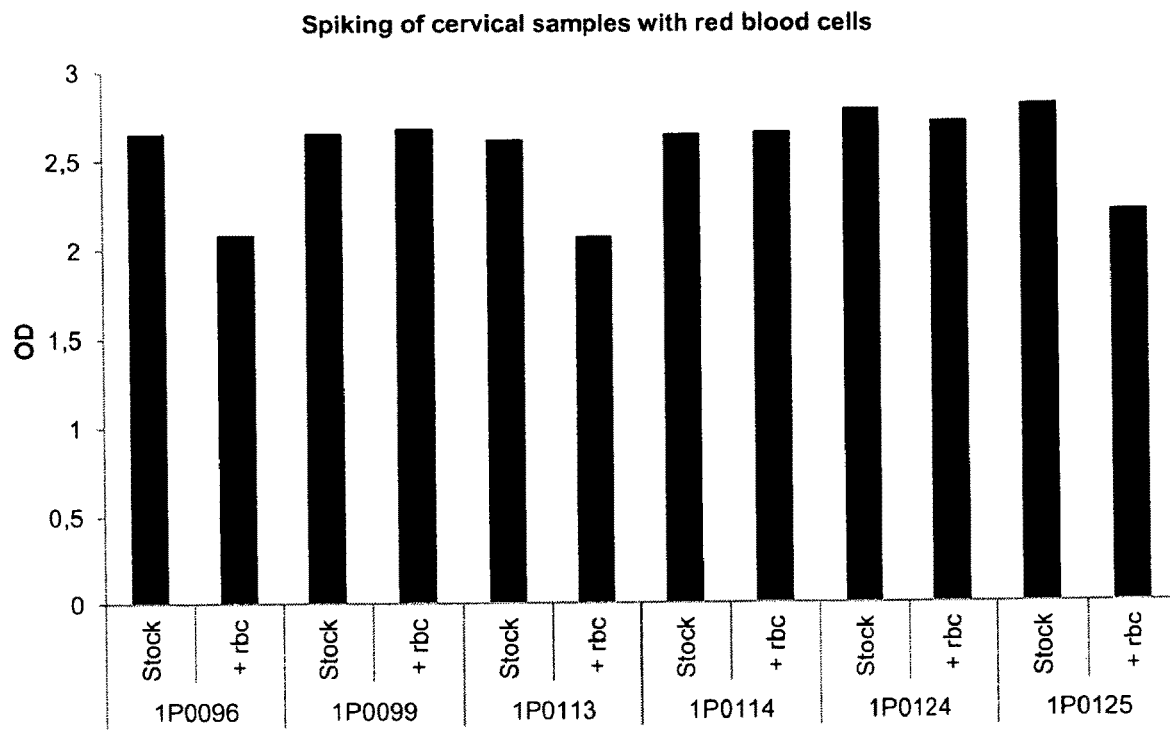
FIGS. 4A and 4B depict the results of the assays described in Example 4.
Figure 4B:
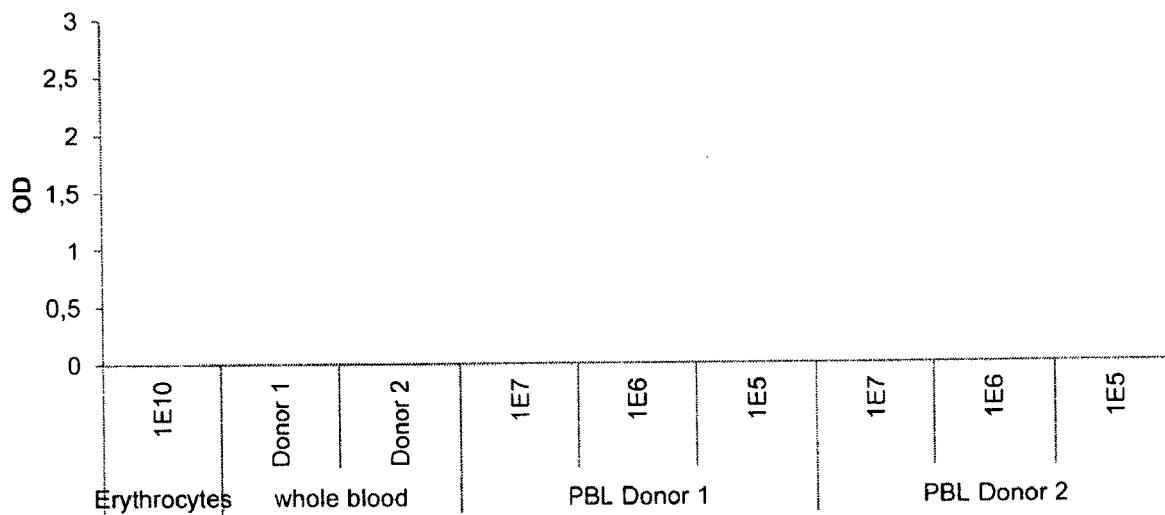

To exclude possible interference caused by non-epithelial components in the cervix, samples such as blood, cervical samples were spiked with red blood cells or whole blood and peripheral blood leucocytes (PBL) alone were tested. For whole blood and PBL alone no detectable signals were measured at all, whereas for cervical samples spiked with red blood cells no negative influence in comparison to the corresponding controls was detectable. Results are shown in FIGS. 4A and 4B.

These data suggest that the setting of the assay is already in the correct dynamic range to detect cytokeratins in cervical samples under physiological as well as pathological conditions.

EXAMPLE 5

Test of Several Alternative Markers for Normalization

Several markers for normalization which were available have been tested. Such marker included DNA, β-actin, Caveolin-1, Human Histone 2A, Human Lamin, Human involucrin. Even though part of such tests is commercially available it turned out that none of the tests could be used successfully for determining the presence or absence of cervical keratinocytes. The results of these experiments are summarized in the following Table 3.

TABLE 3

| Test | Kit | Detection of | Result | Drawbacks |
|---|---|---|---|---|
| Evagreen | — | DNA | Detection in Hela cells and bacteria cells | Not specific to Keratinocytes |
| ß-Actin | Cell signaling technologies | ß-actin | No detection in lysis buffer treated Hela cells | Not specific to Keratinocytes |
| Caveolin-1 | Cell signaling technologies | Caveolin-1 | Detection of lysis buffer treated, ThinPrep-fixed cells | Not specific to Keratinocytes |
| Human Histone 2a | Quayee-Bio | Histone 2a | No measurable results | Not specific to Keratinocytes and Kit failed |
| Human Lamin | Quayee-Bio | Lamin | No measurable results | Not specific to Keratinocytes and Kit failed |

EXAMPLE 6

Figure 5A:
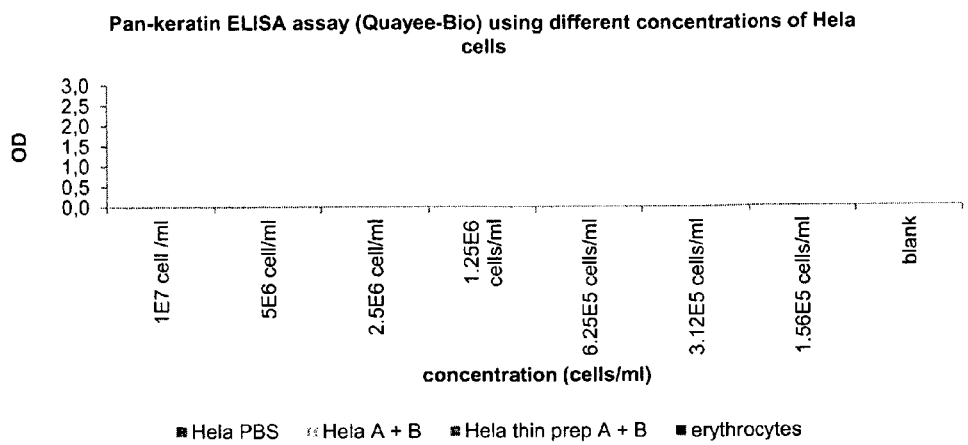
FIGS. 5A, 5B, and 5C depict the results of the testing performed with HeLa cells and clinically characterized samples of patients described in Example 6.
Figure 5B:
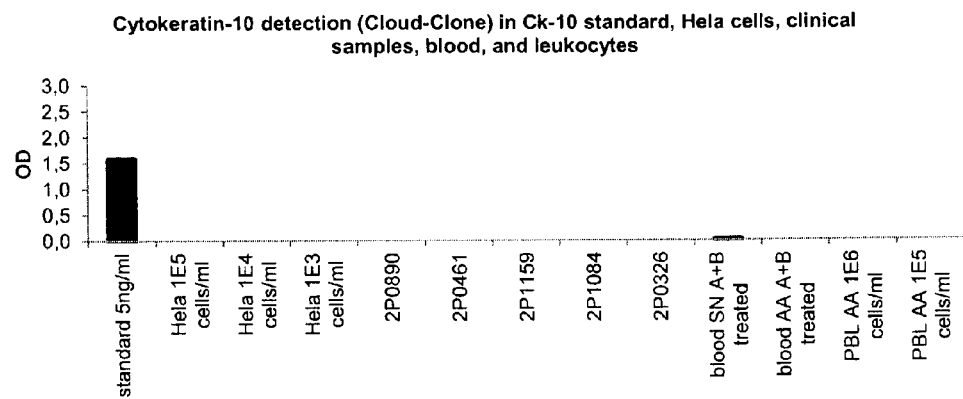
Figure 5C:
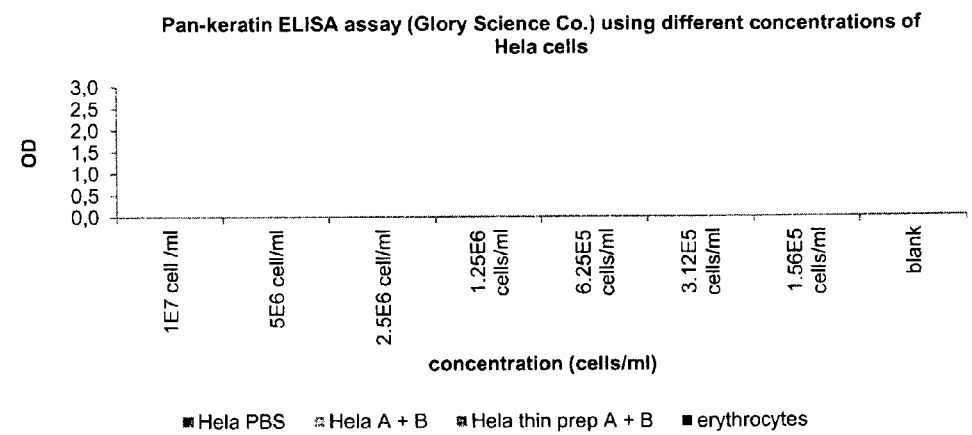
Figure 6A:
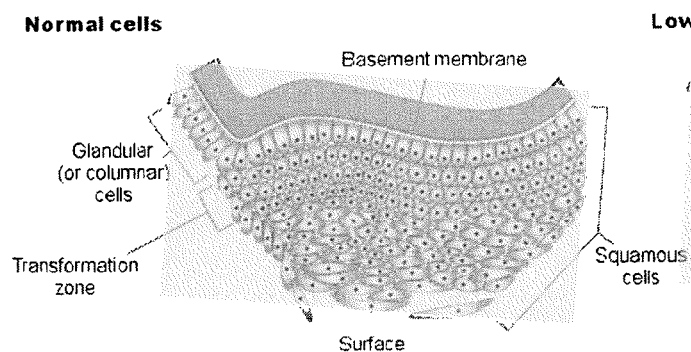
FIGS. 6A to 6D show schematically the transformation of the cervix cells from normal (FIG. 6A) to the malignant state (FIG. 6D), wherein intermediary low-grade and high grade changes are depicted in FIGS. 6B and 6C, respectively.
Figure 6B:
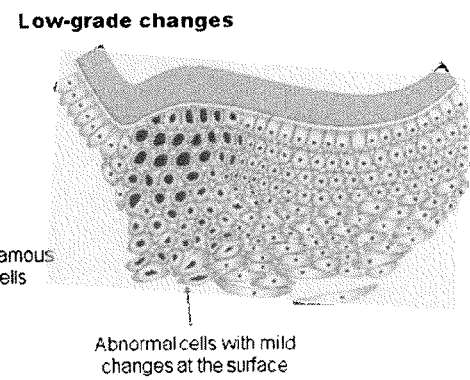
Figure 6C:
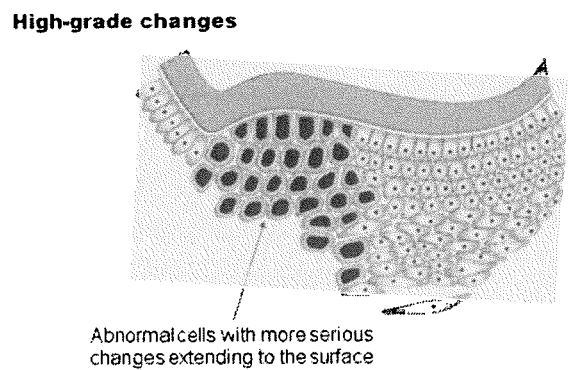
Figure 6D:
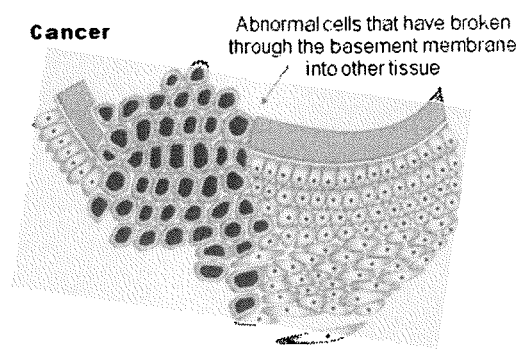

In order to test whether commercially available cytokeratin test kits are suitable for performing a suitable method for standardization, three commercially available cytokeratin test kits, namely the so-called Pan-keratin ELISA assay obtained from Quayee-Bio, the Pan-keratin ELISA assay obtained from Glory Science Co. and the Cytokeratin-10 detection obtained from Cloud-Clone were tested according to the instructions of the manufacturer. The testing was performed with Hela cells and clinically characterized samples of patients. The results are shown in FIGS. 5A-5C. All assays failed since no measurable results for Hela cells or clinical samples could be obtained. Other tests did not show reliable results due to wrong values caused by contamination with other material like blood.

EXAMPLE 7

In order to test the ELISA sandwich test according to the present invention a panel of different patients was tested. The characteristics of the patients are provided in the following Table 4.

TABLE 4

| Patient ID | HPV status | MICROSCOPY special cell characteristics/notes | expected keratin 8, 18, 5 result | actual keratin 8, 18, 5 result |
|---|---|---|---|---|
| W7 | neg | mod sup epis (+clumps) some muc | negative | negative |
| W55 | neg | mod-many sup epis | negative | negative |
| W63 | neg | mod-many sup epis | negative | negative |
| W462 | neg | many sup epis | negative | negative |
| W86 | neg | MANY sup epis, some wbcs | negative | negative |

TABLE 4-continued

| Patient ID | HPV status | MICROSCOPY special cell characteristics/notes | expected keratin 8, 18, 5 result | actual keratin 8, 18, 5 result |
|---|---|---|---|---|
| W431 | neg | MANY sup epis | negative | negative |
| W422 | neg | many sup epis | negative | negative |
| W443 | neg | mod sup epis | negative | negative |
| W104 | neg | sq metaplas, poss parabas cells, poss small EC cell sheets, rare sup epi, occ wbc | positive | positive |
| W405 | neg | 1. sq metaplas, EC/basal cells sheets? Occ parabas cells? | positive | positive |
| W433 | neg | mod-many sup epis, sq metaplas, few-mod parabas cells, some wbcs | positive | Positive |
| W417 | neg | rare sup epis, EC cells? Some parabas cells, occ wbcs | positive | Positive |
| W419 | neg | few sup epis, mod parabas cells, mod large round/int cells, occ wbcs | positive | Positive |
| W426 | neg | EC/basal sheets, poss parabas cells, occ sup epis | positive | Positive |
| W465 | neg | rare sup epis, some parabas, poss sq metaplas, some wbcs | positive | Positive |
| W442 | neg | 2. occ sup epis, occ wbcs, some parabas, sq metaplas? EC sheets? | positive | Positive |
| W460 | neg | occ sup epis, debris, sq metaplas, parabas cells seen | positive | Positive |
| 2P0103 | neg | much super epi debris, poss basal/parabas cell sheets? Endometrial cells? Paraker? Atrophy? | positive | Positive |

The abbreviations in the column headed "Microscopy" have the following meaning:
Occ: occasional
Mod: moderate
Poss: possible
Sup epis: superficial epithelial cells
Parabas: parabasal
EC: endocervical
Int: intermediate
Sq metaplas: squamous metaplasia
Wbcs: white blood cells
Muc: mucus
Paraker: parakeratosis In Table 4 the HPV status of the patients was analyzed. Each of the patients was HPV negative. The samples obtained from the patient were analyzed microscopically and the results are shown in the middle column. The expected results based on the presence or absence of keratins 8, 18 and 5 fully matched with the keratin results measured.

Figure 7A:
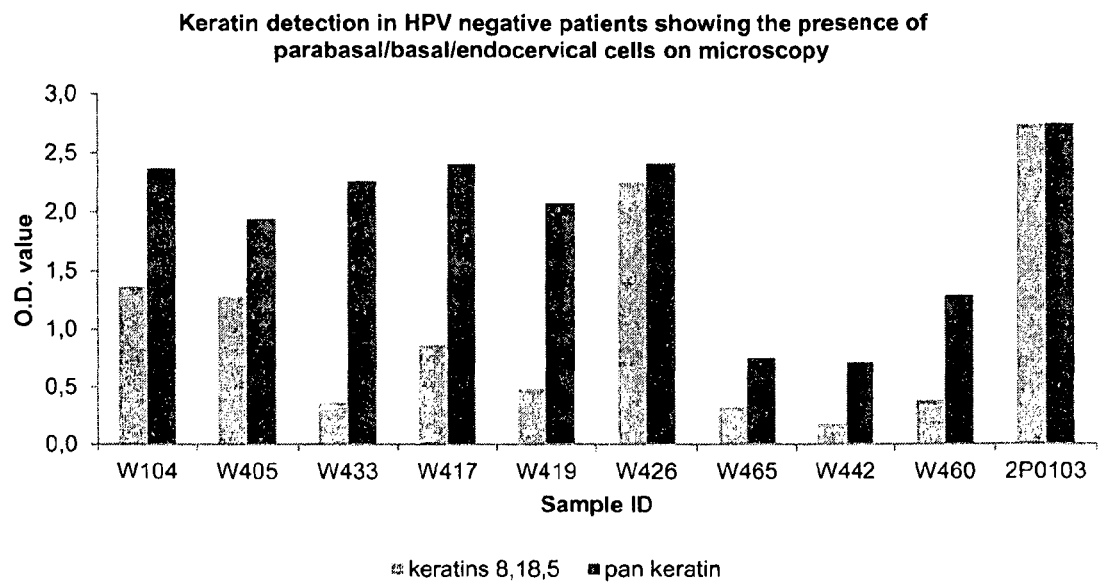
FIGS. 7A and 7B depict the results of the comparison assays of Pan-keratin (all measurable keratins) to the keratins 8, 18 and 5 described in Example 7.
Figure 7B:
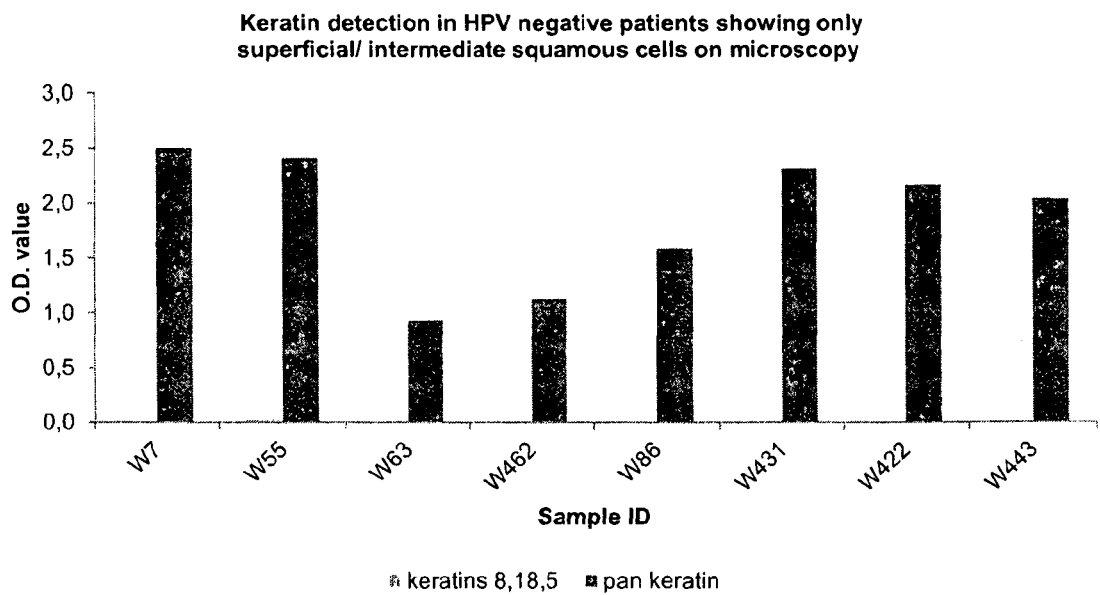

Based on the panel of patients as shown in Table 4 further tests have been performed whereby the Pan-keratin (all measurable keratins) have been compared to the keratins 8, 18 and 5. The result is shown in FIGS. 7A and 7B. Furthermore, the keratin detection in HPV negative patients showing only superficial/intermediate squamous cells were analyzed with microscopy.

The results of these two graphs as shown in FIGS. 7A and 7B, respectively, correlate with microscopy findings: When basal, parabasal, and/or endocervical cells are seen on smear, a signal in the assay is expected for keratins 8, 18, and 5; when none of these cell types are seen on smear, no signal is expected for keratins 8, 18 and 5. Since all samples are taken from otherwise healthy individuals (HPV negative), the data infers that keratins 8, 18, and 5 can be found in undifferentiated squamous cells (basal, parabasal) and/or endocervical cells under normal physiologic conditions.

The experiment provides evidence that keratins 5, 8 and 18 can reliably be used as marker for the presence or absence of the diagnostically relevant cells.

EXAMPLE 8

Figure 8:
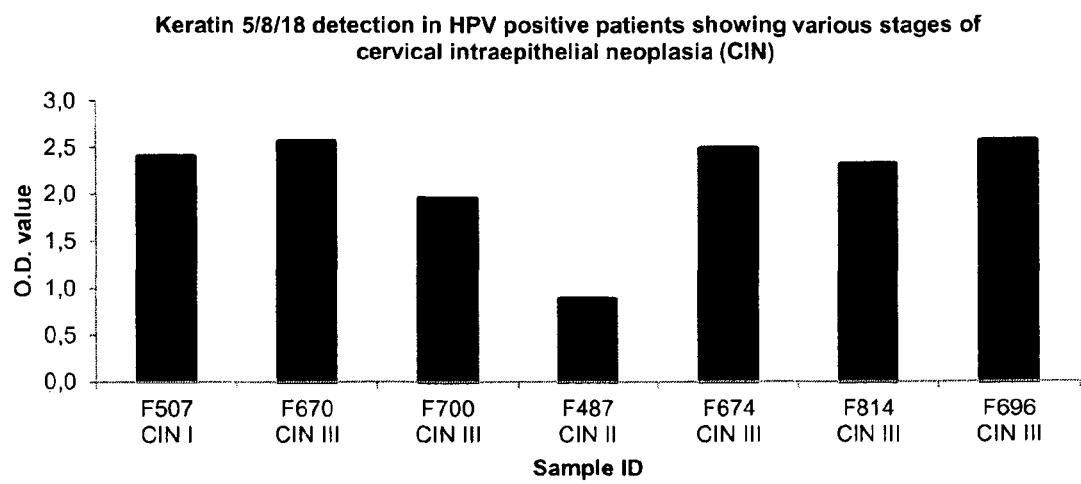
FIG. 8 depicts the results of the tests performed with HPV positive patients showing various stages of cervical intraepithelial neoplasia described in Example 8.

The test of the present invention has also been performed with HPV positive patients showing various stages of cervical intraepithelial neoplasia. The results are shown in FIG. 8. FIG. 8 shows that keratins 8, 18 and 5 can still be detected in the patients designated F507/F696 which show various stages of cervical intraepithelial neoplasia (CIN) suggesting that these keratins are not downregulated through the course of disease progression.

This experiment provides therefore evidence that the preferred keratins 8, 18 and 5 serve as reliable markers for normalization testings.

The data show that the tests disclosed herein reliably detect endocervical/basal/parabasal keratins 5, 8, and 18. The experiments show further that detection is possible in cell lines and cervical specimens, in both healthy patients and those showing various stages of cervical intraepithelial neoplasia. Therefore, a very reliable assay for the detection of a specific subset of cervical keratinocytes in a sample is disclosed, whereby the presence/or absence of keratins 5, 8 and 18 is immunologically tested.

EXAMPLE 9

In order to prove that the method according to the present invention can be suitably used as a normalization test the method has been performed with large panels of different well-characterized samples obtained from the clinic. For each sample a genotyping concerning HPV was performed. Cytologic and histologic data were collected and also coloscopy was performed. By using said measures the disease level was determined and the different samples were categorized as normal patient/HPV negative, normal patient/HPV positive; cervical intraepithelial neoplasia (CIN1, CIN2, CIN3) and carcinoma in situ (CIS) or cervix carcinoma (C×Ca). The results obtained are summarized in the following Table 5:

TABLE 5

| | N = 1518 Normal/ HPV negative | N = 482 Normal/hr HPV positive | N = 2055 Normal total* | N = 340 CIN1 | N = 97 CIN2 | N = 126 CIN3 | N = 19 CIS/CxCa |
|---|---|---|---|---|---|---|---|
| Mean | 1,793 | 1,504 | 1,726 | 1,144 | 1,117 | 1,420 | 1,531 |

CIN Cervical intraepithelial neoplasia
CIS Carcinoma in situ
CxCa Cervix carcinoma
hr high risk
*no infection and infection with HPV high and low risk types Since the mean values obtained with a representative collection of samples are very similar it is evident that the method disclosed herein is suitable to normalize samples obtained from patient, in particular cervical cells obtained by biopsy.

The invention claimed is:

1. A method for confirming the presence of potential oncoprotein-producing target cells in a cell-containing biological sample obtained from a human subject so as to normalize the results of an immunoassay specific for said oncoprotein, said method comprising the step of simultaneously performing:
   a. a first immunological test on said cell-containing biological sample, wherein said first immunological test is a sandwich ELISA that utilizes a capture antibody and a detection antibody to detect and measure the presence of at least three keratins selected from the group consisting of keratin 4, 5, 6, 8, 10, 13, and 18, further wherein each of said capture antibody and said detection antibody is configured to bind to said at least one said three keratins; and
   b. a second immunological test on said same cell-containing biological sample, wherein said second immunological test detects the presence of a biomarker, further wherein said biomarker is an oncoprotein produced by said target cells the presence of which is indicative of cancer;
   wherein the presence of said at least three keratins in said cell-containing biological sample detected and measured by means of step (a) confirms that said cell-containing biological sample in fact contains said target cells and thereby normalizes the results of said second immunological test.

2. The method of claim 1, wherein:
   a. said cell-containing biological sample comprises a cervical sample,
   b. said potential oncoprotein-producing target cells comprise epithelial cells,
   c. said cancer biomarker is HPV oncoprotein E6 and/or HPV oncoprotein E7, and
   d. said at least three keratins include keratins 5, 8 and 18.

3. The method according to claim 1, wherein the capture and the detection antibodies bind specifically to keratins 5, 8 and 18.

4. The method according to claim 1, wherein the capture antibody and the detection antibody are the same antibodies.

5. The method according to claim 1, wherein the capture antibody and the detection antibody are different antibodies.

6. The method according to claim 1, wherein either or both of said capture and detection antibodies are monoclonal antibodies.

7. The method according to claim 1, wherein either or both of said capture and detection antibodies are a mixture of at least two different monoclonal antibodies that bind to different epitopes.

8. The method according to claim 1, wherein either or both of said capture and detection antibodies are polyclonal antibodies.

9. The method according to claim 1, wherein said first immunological test and said second immunological test are performed simultaneously on the same biological sample.

10. The method according to claim 1, wherein the cancer biomarker detected by said second immunological test comprises the oncoprotein E6 and/or the oncoprotein E7 of human papilloma virus.

11. The method according to claim 1, wherein said cell-containing biological sample comprises a cervical sample and said second immunological test comprises an immunoassay for the detection of cervical cancer.

12. The method according to claim 1, wherein said first immunological test and said second immunological test are each performed with an aliquot of the same sample.

* * * * *